(12) United States Patent
Ito et al.

(10) Patent No.: US 7,326,813 B2
(45) Date of Patent: Feb. 5, 2008

(54) PROCESS FOR PRODUCING BENZYLAMINE DERIVATIVE

(75) Inventors: Akinori Ito, Shizuoka (JP); Hideaki Ohashi, Fujieda (JP); Kagetomo Magaribuchi, Shizuoka (JP)

(73) Assignee: Ihara Chemical Industry, Tokyo (JP)

( * ) Notice: Subject to any disclaimer, the term of this patent is extended or adjusted under 35 U.S.C. 154(b) by 45 days.

(21) Appl. No.: 10/540,749

(22) PCT Filed: Dec. 26, 2003

(86) PCT No.: PCT/JP03/16995

§ 371 (c)(1),
(2), (4) Date: Jun. 24, 2005

(87) PCT Pub. No.: WO2004/058681

PCT Pub. Date: Jul. 15, 2004

(65) Prior Publication Data

US 2006/0155141 A1    Jul. 13, 2006

(30) Foreign Application Priority Data

Dec. 26, 2002  (JP) .............................. 2002-376272

(51) Int. Cl.
*C07C 209/62* (2006.01)
*C07C 211/29* (2006.01)
*C07C 231/12* (2006.01)
*C07C 233/31* (2006.01)
*C07C 269/04* (2006.01)

(52) U.S. Cl. ...................................... 564/169; 564/161
(58) Field of Classification Search ..................... None
See application file for complete search history.

(56) References Cited

U.S. PATENT DOCUMENTS

| | | | |
|---|---|---|---|
| 4,566,901 A | 1/1986 | Martin et al. | |
| 4,725,680 A | 2/1988 | Barcelo et al. | |
| 4,968,829 A | 11/1990 | Henrick | |
| 5,663,199 A | 9/1997 | Brouwer | |
| 5,817,814 A | 10/1998 | Konz et al. | |
| 6,531,291 B1 | 3/2003 | Kabbash et al. | |
| 6,812,229 B1 | 11/2004 | Ozaki et al. | |
| 2003/0191146 A1 | 10/2003 | Kabbash et al. | |

FOREIGN PATENT DOCUMENTS

| | | |
|---|---|---|
| EP | 0 155 862 A1 | 9/1985 |
| WO | 01/10825 | 2/2001 |
| WO | 02/062759 A1 | 8/2002 |

OTHER PUBLICATIONS

House H. O. Modern Synthetic Reactions 2nd Edition. py 1972, Benjamin inc. p. 798.*
Cheuk-Man Lee et al.; [(Aminormethyl) aryloxy] acetic Acid Esters. A New Class of High-Ceiling Diuretics. 1. Effects of Nitrogen and Aromatic Nuclear Substitution, Journal of Medicinal Chemistry, 1984, vol. 27, No. 12. pp. 1579 to 1587; compound 50.
Zizhong Li et al; Synthesis of Structurally Identical Fluorine-18 and Iodine Isotope Labeling Compounds for Comparative Imaging, Bioconjugate Chemistry, 2003, vol. 14, No. 2, pp. 287 to 294, Compounds 2, 6, 7, 8, 20, 21.

* cited by examiner

*Primary Examiner*—Yvonne Eyler
*Assistant Examiner*—Yevgeny Valenrod
(74) *Attorney, Agent, or Firm*—Arent Fox LLP

(57) ABSTRACT

Disclosed is a process for producing a benzylamine derivative represented by the general formula (3):

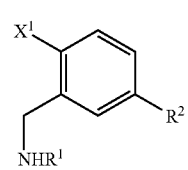

(3)

wherein $X^1$, $R^1$ and $R^2$ are as defined below, which comprises reacting a benzyl derivative represented by the general formula (1):

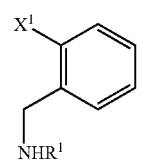

(1)

wherein $X^1$ represents a halogen atom and $R^1$ represents an acyl group, with a haloacyl compound represented by the general formula (2):

$$R^2-X^2 \qquad (2)$$

wherein $X^2$ represents a halogen atom and $R^2$ represents an acyl group, in the presence of Lewis acid. According to this method, a benzylamine derivative as an intermediate, which is useful for the preparation of a carbamate-based agricultural or horticultural bactericide, can be preferably prepared.

5 Claims, No Drawings

PROCESS FOR PRODUCING BENZYLAMINE DERIVATIVE

TECHNICAL FIELD

The present invention relates to a process for producing a benzylamine derivative, process for producing a carbamate derivative via the method, and a useful intermediate in the process for producing a carbamate derivative. The benzylamine derivative obtained by the present invention serves as an intermediate which is useful for the preparation of a carbamate-based agricultural or horticultural bactericide.

BACKGROUND ART

As a process for producing a carbamate-based agricultural or horticultural bactericide, for example, there have hitherto been known (i) a process for producing a bactericide, which comprises reacting a carbamate derivative represented by the general formula (6) described hereinafter with hydroxylamine or a derivative thereof (see Preparation Method 1 of Patent Document 1); and (ii) a process for producing a bactericide, which comprises halogenating a toluene derivative to give an α-halo-substituted toluene derivative, reacting with potassium cyanate thereby to carbamate the toluene derivative, introducing a nitro group and converting the nitro group into an amino group, followed by diazotization and further reaction with an oxime compound (see Chemical Formula 11 and Preparation method 5 of Patent Document 1).

Among these methods (i) and (ii), the method (i) is considered to be preferable in the industrial preparation in view of safety because it is conducted via no diazotization, in addition to yield, safety of the reaction and ease of work and operation (see Preparation Examples 3 and 6 of Patent Document 1).

A carbamate derivative represented by the general formula (6) described hereinafter used in the method (i) is prepared by a known method, for example, a method comprising halogenating a toluene derivative having an acyl group to give an α-halo-substituted toluene derivative having an acyl group, and reacting with potassium cyanate thereby to carbamate the toluene derivative (see [Chemical Formula 8] of Patent Document 1) or a method comprising halogenating a toluene derivative having an alkoxycarbonyl group to give an α-halo-substituted toluene derivative having an alkoxycarbonyl group, reacting the toluene derivative with potassium cyanate thereby to introduce a carbamate group, and converting the alkoxycarbonyl group as a functional group into an acyl group (see [Chemical Formula 9] of Patent Document 1).

However, according to the former method described in [Chemical Formula 8] of Patent Document 1, a position isomer is produced as by-product in the preparation of a toluene derivative having an acyl group as a raw material because of low regioselectivity in case of nuclear introduction of an acyl group, and thus a decrease in yield of the objective toluene derivative having an acyl group can not be avoided. Also the latter method described in [Chemical Formula 9] of Patent Document 1 had a problem in that each step requires comparatively long time and a carbamate group itself is exposed to severe conditions in an acid or base and thus the carbamate group can not be stably maintained and is decomposed under the reaction conditions. Furthermore, it was required for any method to improve insufficient yield in entire steps from a raw material.

Patent Document 1: Japanese Unexamined Patent Publication (Kokai) No. 2001-106666

Therefore, it was required to solve the above problems of the prior art and to develop a method and a novel intermediate, which are useful for the preparation of a novel carbamate derivative.

DISCLOSURE OF THE INVENTION

An object of the present invention is to solve the problems of the prior art and to develop a method which is useful for the preparation of a carbamate derivative.

An object of the present invention is to solve the problems of the prior art and to develop an intermediate which is useful for the preparation of a carbamate derivative.

The present inventors have intensively studied and found that, when an acyl group is introduced into a benzyl compound (benzyl derivative) having a protected amino group, the acyl group is introduced with high regioselectivity to obtain a novel benzylamine derivative, surprisingly.

The present inventors have further studied based on the above discovery and found that a carbamate derivative represented by the general formula (6) described hereinafter can be prepared without producing an isomer, substantially, when the novel benzylamino derivative is reacted with a haloformic acid ester after amino deprotection with hydrolysis, and also found that such a method is extremely useful to attain desired improvement in the above-mentioned prior art. Thus, the present invention has been completed.

The present invention includes, for example, the following aspects [1] to [25].

[1] A process for producing a benzylamine derivative represented by the general formula (3):

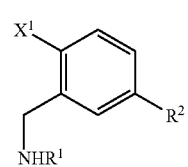

(3)

wherein $X^1$, $R^1$ and $R^2$ are as defined below, which comprises reacting a benzyl derivative represented by the general formula (1):

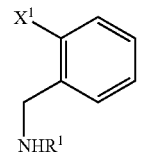

(1)

wherein $X^1$ represents a halogen atom and $R^1$ represents an acyl group, with a haloacyl compound represented by the general formula (2):

$$R^2-X^2 \quad (2)$$

wherein $X^2$ represents a halogen atom and $R^2$ represents an acyl group, in the presence of Lewis acid.

[2] A process for producing a carbamate derivative represented by the general formula (6):

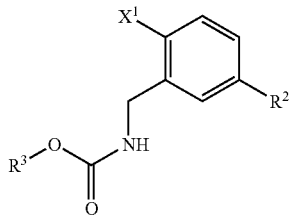  (6)

wherein $X^1$, $R^2$ and $R^3$ are as defined below, which comprises reacting a benzyl derivative represented by the general formula (1):

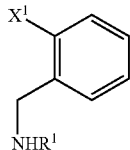  (1)

wherein $X^1$ represents a halogen atom and $R^1$ represents an acyl group, with a haloacyl compound represented by the general formula (2):

  (2)

wherein $X^2$ represents a halogen atom and $R^2$ represents an acyl group, in the presence of Lewis acid to obtain a benzylamine derivative represented by the general formula (3):

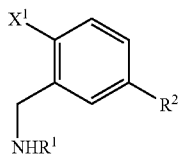  (3)

wherein $X^1$, $R^1$ and $R^2$ are as defined above, hydrolyzing the benzylamine derivative to obtain an amino derivative represented by the general formula (4):

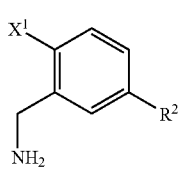  (4)

wherein $X^1$ and $R^2$ are as defined above, and reacting the amino derivative with a haloformic acid ester represented by the general formula (5):

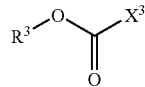  (5)

wherein $X^3$ represents a halogen atom and $R^3$ represents an alkyl group, in the presence of a base.

[3] An acylbenzylamine derivative represented by the general formula (7);

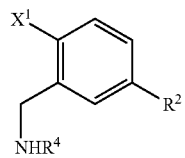  (7)

wherein $X^1$ represents a halogen atom, $R^2$ represents an acyl group, and $R^4$ represents a hydrogen atom or an acyl group.

[4] The process for producing a benzylamine derivative according to [1], wherein $X^1$ is a chlorine atom.

[5] The process for producing a benzylamine derivative according to [1], wherein $R^1$ is an aliphatic acyl group.

[6] The process for producing a benzylamine derivative according to [1], wherein $X^1$ is a chlorine atom and $R^1$ is an aliphatic acyl group.

[7] The process for producing a benzylamine derivative according to [1], wherein $X^1$ is a chlorine atom and $R^1$ is an aliphatic acyl group having 1 to 7 carbon atoms.

[8] The process for producing a benzylamine derivative according to [1], wherein $X^1$ is a chlorine atom and $R^1$ is an acetyl group.

[9] The process for producing a carbamate derivative according to [2], wherein $X^1$ is a chlorine atom.

[10] The method for preparing a carbamate derivative according to [2], wherein $R^1$ is an aliphatic acyl group.

[11] The process for producing a carbamate derivative according to [2], wherein $X^1$ is a chlorine atom and $R^1$ is an aliphatic acyl group.

[12] The process for producing a carbamate derivative according to [2], wherein $X^1$ is a chlorine atom and $R^1$ is an aliphatic acyl group having 1 to 7 carbon atoms.

[13] The process for producing a carbamate derivative according to [2], wherein $X^1$ is a chlorine atom and $R^1$ is an acetyl group.

[14] The process for producing a carbamate derivative according to [2], wherein $X^2$ is a chlorine atom.

[15] The method for preparing a carbamate derivative according to [2], wherein $R^2$ is an aliphatic acyl group.

[16] The process for producing a carbamate derivative according to [2], wherein $X^2$ is a chlorine atom and $R^2$ is an aliphatic acyl group.

[17] The process for producing a carbamate derivative according to [2], wherein $X^2$ is a chlorine atom and $R^2$ is an aliphatic acyl group having 1 to 7 carbon atoms.

[18] The process for producing a carbamate derivative according to [2], wherein $X^2$ is a chlorine atom and $R^2$ is an acetyl group.

[19] The process for producing a carbamate derivative according to [2], wherein $X^1$ and $X^2$ are chlorine atoms and $R^1$ and $R^2$ are aliphatic acyl groups having 1 to 7 carbon atoms.

[20] The process for producing a carbamate derivative according to [2], wherein $X^1$ and $X^2$ are chlorine atoms and $R^1$ and $R^2$ are acetyl groups.

[21] The process for producing a carbamate derivative according to [2], wherein $X^1$ and $X^2$ are chlorine atoms, $R^1$ and $R^2$ are acetyl groups, and the base is potassium carbonate.

[22] The process for producing an acylbenzylamine derivative according to [3], wherein $X^1$ is a chlorine atom and $R^1$ is an aliphatic acyl group having 1 to 7 carbon atoms.

[23] The process for producing an acylbenzylamine derivative according to [3], wherein $X^1$ is a chlorine atom and $R^2$ is an aliphatic acyl group having 1 to 7 carbon atoms.

[24] The process for producing an acylbenzylamine derivative according to [3], wherein $X^1$ is a chlorine atom and $R^1$ and $R^2$ are aliphatic acyl groups having 1 to 7 carbon atoms.

[25] The process for producing an acylbenzylamine derivative according to [3], wherein $X^1$ is a chlorine atom and $R^1$ and $R^2$ are acetyl groups.

The method [1] is characterized in that an acyl group ($R^2$) is introduced into the position (5-position) represented by the general formula (3) highly selectively (that is, high position regioselectivity) in the reaction of the benzyl derivative represented by the general formula (1) with the haloacyl compound represented by the general formula (2) and thus a position isomer is not substantially produced as by-product. Therefore, the method is extremely useful in the industrial preparation of the objective product. The carbamate derivative represented by the general formula (6) is a compound which is useful as an intermediate of the above carbamate-based bactericide (see Japanese Unexamined Patent Publication (Kokai) No. 2001-106666).

In the reaction of the benzyl derivative represented by the general formula (1) with the haloacyl compound represented by the general formula (2), there can be obtained a benzylamine derivative (3) wherein $R^2$ is introduced into the objective 5-position, in a GC area percentage of preferably at least 15, and more preferably about 45 to 50, in case the total GC area relative to a compound wherein $R^2$ is introduced into the position except for the 5-position is 1.

BEST MODE FOR CARRYING OUT THE INVENTION

The present invention will now be described in detail with reference to the drawings, as desired. In the following descriptions, parts and percentages, which indicate quantitative ratio, are by weight unless otherwise specified.

(Present Invention (1))

First, the method of the present invention [1] will be described.

The process [1] of the present invention is a process for producing a benzylamine derivative represented by the general formula (3) by reacting a benzyl derivative represented by the general formula (1) with a haloacyl compound represented by the general formula (2) in the presence of Lewis acid. The method is characterized in that an acyl group is introduced into the position (5-position) represented by the general formula (3) highly selectively in this reaction and is useful in industrial use.

For example, the acyl group as $R^1$ in the general formula (1) may be an aliphatic acyl group, an alicyclic acyl group, or an aromatic acyl group.

(Aliphatic Acyl Group)

The aliphatic acyl group ($R^1$) may be either of a linear aliphatic acyl group and a branched aliphatic acyl group, and also may contain an unsaturated bond in an aliphatic residue or may be substituted with an alicyclic group such as alicyclic alkyl group.

The alicyclic acyl group includes, for example, linear or branched aliphatic acyl groups having 1 to 7 carbon atoms (for example, the number of carbon atoms is abbreviated to "$C_1$-$C_7$" in this case) and specific examples thereof include formyl group, acetyl group, propionyl group, 2-propionyl group, butyryl group, isobutyryl group, pentanoyl group, hexanoyl group, allylcarbonyl group, and cyclohexylmethylcarbonyl group.

(Alicyclic Acyl Group)

The alicyclic group ($R^1$) may contain an unsaturated bond in an alicyclic residue. Such an alicyclic acyl group includes, for example, $C_3$-$C_6$ cycloalkylcarbonyl groups and specific examples thereof include cyclopropylcarbonyl group, cyclopentylcarbonyl group, cyclohexylcarbonyl group, and 1-cyclohexenylcarbonyl group.

(Aromatic Acyl Group)

The aromatic acyl group ($R^1$) may be substituted with an alkyl or alkoxy group. Such an aromatic acyl group includes, for example, aromatic acyl groups such as benzoyl group, 4-methylbenzoyl group, and 4-methoxybenzoyl group.

$R^1$ of the benzyl derivative represented by the general formula (1) is preferably an aliphatic acyl group, more preferably a $C_1$-$C_7$ aliphatic acyl group, and particularly preferably an acetyl group, in view of the yield of the objective product in the reaction with the haloacyl compound represented by the general formula (2) and reactivity in the subsequent process.

(Halogen Atom)

$X^1$ in the general formula (1) represents a halogen atom and specific examples thereof include fluorine atom, chlorine atom, bromine atom, and iodine atom.

(Examples of Benzyl Derivative)

Examples of the benzyl derivative represented by the general formula (1) include N-[(2-chlorophenyl)methyl]acetamide, N-[(2-bromophenyl)methyl]acetamide, N-[(2-fluorophenyl)methyl]acetamide, N-[(2-chlorophenyl)methyl]propanamide, N-[(2-bromophenyl)methyl]propanamide, N-[(2-fluorophenyl)methyl]propanamide, N-[(2-chlorophenyl)methyl]-2-methylpropanamide, N-[(2-bromophenyl)methyl]-2-methylpropanamide, N-[(2-fluorophenyl)methyl]-2-methylpropanamide, N-[(2-chlorophenyl)methyl]-2-methylbutanamide, N-[(2-bromophenyl)methyl]-2-methylbutanamide, N-[(2-fluorophenyl)methyl]-2-methylbutanamide, N-[(2-chlorophenyl)methyl]benzamide, N-[(2-bromophenyl)methyl]benzamide, and N-[(2-fluorophenyl)methyl]benzamide.

These benzyl derivatives represented by the general formula (1) are known compounds or compound which can be synthesized by the method of reacting a corresponding 2-halogenobenzylamine compound with a corresponding acid anhydride or acid chloride.

(Acyl Group)

For example, the acyl group ($R^2$) in the general formula (2) is preferably an aliphatic acyl group, an alicyclic acyl group, or an aromatic acyl group.

(Aliphatic Acyl Group)

The aliphatic acyl group ($R^2$) may be either of a linear aliphatic acyl group and a branched aliphatic acyl group, and also may contain an unsaturated bond in an aliphatic residue or may be substituted with an alicyclic group such as alicyclic alkyl group. Such an aliphatic acyl group includes, for example, $C_1$-$C_7$ linear or branched aliphatic acyl groups and specific examples thereof include formyl group, acetyl group, propionyl group, 2-propionyl group, butyryl group, isobutyryl group, pentanoyl group, hexanoyl group, allylcarbonyl group, and cyclohexylmethylcarbonyl group.

(Alicyclic Acyl Group)

The alicyclic group ($R^2$) may contain an unsaturated bond in an alicyclic residue. Such an alicyclic acyl group includes, for example, $C_3$-$C_6$ cycloalkylcarbonyl groups and specific examples thereof include cyclopropylcarbonyl group, cyclopentylcarbonyl group, cyclohexylcarbonyl group, and 1-cyclohexenylcarbonyl group.

The aromatic acyl group ($R^2$) may be substituted with an alkyl or alkoxy group. Such an aromatic acyl group includes, for example, aromatic acyl groups such as benzoyl group, 4-methylbenzoyl group, and 4-methoxybenzoyl group.

$R^2$ of the haloacyl compound represented by the general formula (2) is preferably an aliphatic acyl group, more preferably a $C_1$-$C_7$ aliphatic acyl group, and particularly preferably an acetyl group, in view of the yield of the objective product.

(Halogen Atom)

$X^2$ in the general formula (2) represents a halogen atom and specific examples thereof include fluorine atom, chlorine atom, bromine atom, and iodine atom.

(Examples of Haloacyl Compound)

Examples of the haloacyl compound represented by the general formula (2) include acetyl chloride, acetyl bromide, propionyl chloride, butyryl chloride, isobutyryl chloride, valeryl chloride, isovaleryl chloride, t-butylacetyl chloride, and 2-ethylbutyryl chloride.

The haloacyl compound represented by the general formula (2) is a known compound, or can be synthesized, for example, by chlorinating the corresponding carboxylic acid with thionyl chloride.

(Amount)

The amount of the haloacyl compound represented by the general formula (2) to be reacted with 1 mole of the benzyl compound represented by the general formula (1) is not specifically limited. The amount of the haloacyl compound is usually within a range from 1.0 to 2.0 moles, preferably from 1.0 to 1.5 moles, and more preferably from 1.0 to 1.2 moles.

(Lewis Acid)

In the present invention, the above reaction is conducted in the presence of Lewis acid, Examples of the Lewis acid used in the reaction include metal halides such as aluminum chloride ($AlCl_3$), zinc chloride ($ZnCl_2$), and iron(III) chloride ($FeCl_3$). Among these metal halides, aluminum chloride ($AlCl_3$) is preferably used. The amount of the Lewis acid used in the reaction is within a range from 2.0 to 5.0 moles, and preferably from 2.5 to 3.0 moles, based on 1 mole of the benzyl compound represented by the general formula (1).

(Solvent)

The reaction can be sufficiently conducted with or without using a solvent. The solvent, which can be used in the reaction, may be any solvent which does not substantially inhibit the reaction. Examples of the solvent include aromatic hydrocarbons which may be substituted with at least one nitro group or halogen, such as nitrobenzene, dichlorobenzene and trichlorobenzene; and halogenated aliphatic hydrocarbons such as dichloromethane, dichlorethane, and chloroform. Among these solvents, halogenated aliphatic hydrocarbons such as dichloromethane are preferable. These solvents can be used alone or used as a solvent mixture in any mixing ratio.

The amount of the solvent may be the amount which enables sufficient stirring of the reaction system, and is usually within a range from 0.1 to 2.0 L (liters), preferably from 0.3 to 1.0 L, and more preferably from 0.3 to 0.8 L, based on 1 mole of the benzylamine compound represented by the general formula (1).

(Reaction Temperature and Time)

The reaction temperature may be within a range from 20° C. to a reflux temperature of the solvent used, preferably from 30 to 80° C., and more preferably from 40 to 60° C.

The reaction time is not specifically limited, but is preferably from 6 to 24 hours, in view of inhibition of the production of by-products.

(Benzylamine Derivative)

The benzylamine derivative represented by the general formula (3) obtained by the reaction is a compound which is useful as an intermediate material used to prepare various compounds (for example, carbamate derivative represented by the general formula (6)).

(Present Invention [2])

Subsequently, the present invention [2] will be described.

The present invention [2] is directed to a method for preparing a carbamate derivative represented by the general formula (6) via the method of the present invention [1]. According to this method, a benzylamine derivative represented by the general formula (3) is prepared by reacting a benzyl compound represented by the general formula (1) with a haloacyl compound represented by the general formula (2) in the presence of Lewis acid and a carbamate derivative represented by the general formula (6) is prepared by reacting an amino compound represented by the general formula (4) obtained by hydrolyzing the benzylamine derivative represented by the general formula (3) with a haloformic acid ester represented by the general formula (5) in the presence of a base.

The benzylamine derivative represented by the general formula (3) is prepared in the same manner as in case of [1].

(Hydrolysis)

The preparation of the amino derivative represented by the general formula (4) by hydrolysis of the benzylamine derivative represented by the general formula (3) obtained in the present invention [1] will now be described.

The method for hydrolysis of the benzylamine derivative represented by the general formula (4) is not specifically limited, but is preferably conducted using Broensted acid in view of ease of handling.

(Broensted Acid)

Examples of the Broensted acid, which can be used in the hydrolysis reaction, include aliphatic carboxylic acids which may be substituted with halogen, such as acetic acid, propionic acid, and trifluoroacetic acid; and mineral acids such as sulfuric acid and hydrochloric acid. Among these acids, mineral acids are preferable and sulfuric acid is particularly preferable. More specifically, the reaction may be conducted using 20 to 80%, preferably 40 to 80% sulfuric acid. The amount of the Broensted acid used in the reaction may be within a range from 1.0 to 5.0 moles, and preferably from 2.0 to 3.0 moles, based on 1 mole of the acyl derivative represented by the general formula (3).

(Water)

The amount of water used in the reaction may be at last a stoichiometric amount, and specifically at least 1 moles, based on 1 mole of the benzylamine derivative represented by the general formula (3).

(Solvent)

The reaction can be sufficiently conducted with or without using a solvent. The solvent, which can be used in the reaction, may be any solvent which does not substantially inhibit the reaction. Examples of the solvent include aromatic hydrocarbons which may be substituted with at least one $C_1$-$C_6$ alkyl group or halogen, such as toluene, xylene, chlorobenzene, dichlorobenzene, and trichlorobenzene. Among these solvents, trichlorobenzene is preferable. These solvents can be used alone or used as a solvent mixture in any mixing ratio. The amount of the solvent may be the amount which enables sufficient stirring of the reaction system, and is usually within a range from 0.05 to 0.5 L, preferably from 0.1 to 0.3 L, and more preferably from 0.1 to 0.2 L, based on 1 mole of the benzylamine compound represented by the general formula (3).

(Reaction Temperature and Time)

The reaction temperature may be within a range from 70° C. to a reflux temperature of the solvent used, preferably from 80 to 130° C., and more preferably from 100 to 110° C.

The reaction time is not specifically limited, but is preferably from 5 to 15 hours, in view of inhibition of the production of by-products.

(Reaction for Preparation of Carbamate Derivative)

The reaction of an amino derivative represented by the general formula (4) thus obtained with a haloformic acid ester represented by the general formula (5) to obtain a carbamate derivative represented by the general formula (6) will now be described.

(Haloformic Acid Ester)

$R^3$ in the haloformic acid ester represented by the general formula (5) is an alkyl group. For example, the alkyl group is preferably a linear or branched $C_1$-$C_7$ alkyl group such as methyl group, ethyl group, n-propyl group, isopropyl group, n-butyl group, sec-butyl group, t-butyl group, n-pentyl group, or n-hexyl group.

(Halogen Atom)

$X^3$ in the general formula (5) represents a halogen atom, for example, fluorine atom, chlorine atom, bromine atom, or iodine atom.

(Haloformic Acid Ester)

Therefore, specific examples of the haloformic acid ester represented by the general formula (5), which can be used in the reaction, include methyl chloroformate, ethyl chloroformate, n-propyl chloroformate, isopropyl chloroformate, n-butyl chloroformate, and isobutyl chloroformate.

The haloformic acid ester represented by the general formula (5) is a known compound (therefore, it can also be obtained by a known reaction, if necessary).

The reaction of the amino derivative represented by the general formula (4) with the haloformic acid ester represented by the general formula (5) proceeds at any molar ratio. The amount of the haloformic acid ester represented by the general formula (5) is usually within a range from 1.0 to 2.0 moles, preferably from 1.0 to 1.5 moles, and more preferably from 1.0 to 1.2 moles, based on 1 mole of the amino derivative represented by the general formula (4).

(Base)

The reaction is conducted using a base. Examples of the base, which can be used in the reaction, include organic bases typified by tertiary amines such as triethylamine and diisopropylethylamine; alkali metal carbonates such as potassium carbonate and sodium carbonate; and alkali metal hydroxides such as potassium hydroxide and sodium hydroxide. This base is preferably an alkali metal carbonate, and particularly preferably potassium carbonate. The amount of the base used in the reaction may be within a range from 1.0 to 3.0 moles, and preferably from 1.1 to 1.5 moles, based on 1 mole of the amino derivative represented by the general formula (4).

(Solvent)

The reaction can be sufficiently conducted with or without using a solvent. The solvent, which can be used in the reaction, may be any solvent which does not substantially inhibit the reaction. Examples of the solvent include aromatic hydrocarbons which may be substituted with at least one alkyl group or halogen, such as toluene, xylene, and chlorobenzene; halogenated aliphatic hydrocarbons such as dichloromethane and chloroform; acetic acid esters such as methyl acetate, ethyl acetate, and butyl acetate; aprotic polar solvents such as dimethylformamide, dimethylacetamide, N-methyl pyrrolidone, tetramethyl urea and, hexamethylphosphoric triamide (HMPA); and ether-based solvents such as diethyl ether, tetrahydrofuran (THF), and dioxane.

Among these solvents, aromatic hydrocarbons are preferable and toluene is particularly preferable. These solvents can be used alone or used as a solvent mixture in any mixing ratio. The amount of the solvent may be the amount which enables sufficient stirring of the reaction system, and is usually within a range from 0.2 to 2.0 L, and preferably from 0.5 to 1.0 L, based on 1 mole of the amino derivative represented by the general formula (4).

(Reaction Temperature and Time)

The reaction temperature may be within a range from 0° C. to a reflux temperature of the solvent used, preferably from 10 to 80° C., and more preferably from 20 to 60° C.

The reaction time is not specifically limited, but is preferably from 0.5 to 6 hours, in view of inhibition of the production of by-products.

(Carbamate Derivative)

The carbamate derivative represented by the general formula (6) obtained by the present invention [2] is a compound which is useful as an intermediate material used to prepare various compounds (for example, carbamate-based agrochemicals (particularly bactericide)).

(Amino-Protected Substituted Compound)

various amino-protected substituted compounds can also be prepared by reacting the amino derivative represented by the general formula (4) obtained as described above with known reagents used generally to protect an amino group [for example, formic acid ester reagents such as benzyl chloroformate and di-t-butyl dicarbonate; acid halide reagents such as propionyl chloride; halogenated alkyl reagents such as ethyl chloride; and 2-(t-butoxycarbonyloxyimino)-2-phenylacetonitrile].

Examples of the amino-protected substituted compound include various amino-protected substituted compounds in which an amino group is protected with a known protecting group, for example, (i) urethane type protecting group (R=BOC group (t-butoxycarbonyl), Cbz group (benzyloxycarbonyl), Cbz (OMe) group (p-methoxybenzyloxycarbonyl), Cbz (Cl) group (p-chlorobenzyloxycarbonyl), or Cbz (NO$_2$) group (p-nitrobenzyloxycarbonyl), (ii) acyl type protecting group (formyl group, acetyl group, propionyl group, butyryl group, pentynyl group, or hexenyl group in the compound (1) of the present invention, or (iii) alkyl type protecting group ($C_1$-$C_6$ linear or branched alkyl group such as methyl group, ethyl group, n-propyl group, isopropyl group, n-butyl group, sec-butyl group, t-butyl group, n-pentyl group, or n-hexyl group).

Already known method can be applied to the synthesis of the amino-protected substituted compound.

(Present Invention [3])

The compound according to [3] of the present invention is an acylbenzylamine derivative represented by the general formula (7).

(Acylbenzylamine Derivative)

The acylbenzylamine derivative represented by the general formula (6) according to [3] of the present invention includes a benzylamine derivative represented by the general formula (3) and an amino derivative represented by the general formula (4), which are obtained in [1] and [2] of the present invention. As described above, these derivatives are compounds which are useful as a raw material of a carbamate derivative represented by the general formula (6), serving as an intermediate used to prepare various compounds (carbamate-based compounds which are known to be useful as agrochemicals).

(Substituent)

In the general formula (7), the substituent $X^1$ represents a halogen atom, for example, a fluorine atom, a chlorine atom, a bromine atom, or an iodine atom.

In the general formula (7), the substituent $R^4$ represents a hydrogen atom or the same acyl group as that of $R^2$. The same acyl group as that of $R^2$ may be, for example, an aliphatic acyl group, an alicyclic acyl group or an aromatic acyl group.

(Aliphatic Acyl Group)

The aliphatic acyl group ($R^4$) may be either of a linear aliphatic acyl group and a branched aliphatic acyl group. The aliphatic acyl group may contain an unsaturated bond in an aliphatic residue and also may be substituted with an alicyclic group such as alicyclic alkyl group. Examples of the aliphatic acyl group include $C_1$-$C_7$ linear or branched aliphatic acyl groups, for example, formyl group, acetyl group, propionyl group, 2-propionyl group, butyryl group, isobutyryl group, pentanoyl group, hexanoyl group, allylcarbonyl group, and cyclohexylmethylcarbonyl group.

(Alicyclic Acyl Group)

The alicyclic acyl group ($R^4$) may contain an unsaturated bond in an aliphatic residue. Examples of the alicyclic acyl group include $C_3$-$C_6$ cycloalkylcarbonyl groups, for example, cyclopropylcarbonyl group, cyclopentylcarbonyl group, cyclohexylcarbonyl group, and 1-cyclohexenylcarbonyl group.

(Aromatic Acyl Group)

The aromatic acyl group ($R^4$) may be substituted with an alkyl group or an alkoxy group. Examples of the aromatic acyl group include aromatic acyl group, for example, benzoyl group, 4-methylbenzoyl group, and 4-methoxybenzoyl group.

(Specific Examples of Compound of the Present Invention)

Specific examples of the compound of the present invention which has these substituents $X^1$, $R^2$ and $R^4$ include, but are not limited to, those described in Table 1. The compound number is referred to the following description. Abbreviations in (Table 1) have the following meanings.

Ac: Acetyl group

Prn: Propionyl group

TABLE 1

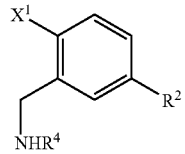

(7)

| Compound No. | $X^1$ | $R^2$ | $R^4$ |
|---|---|---|---|
| 1 | Cl | Ac | H |
| 2 | Cl | Prn | H |
| 3 | Cl | Ac | Ac |
| 4 | Cl | Prn | Ac |
| 5 | Cl | Ac | Prn |
| 6 | Cl | Prn | Prn |
| 7 | Br | Ac | H |
| 8 | Br | Prn | H |
| 9 | Br | Ac | Ac |
| 10 | Br | Prn | Ac |
| 11 | Br | Ac | Prn |
| 12 | Br | Prn | Prn |
| 13 | F | Ac | H |
| 14 | F | Prn | H |
| 15 | F | Ac | Ac |
| 16 | F | Prn | Ac |
| 17 | F | Ac | Prn |
| 18 | F | Prn | Prn |

Examples of preferable intermediate of the carbamate derivative (6), which is used an intermediate of an agricultural or horticultural bactericide, include a compound 1 in which $X^1$ is Cl, $R^2$ is Ac (acetyl group) and $R^4$ is H (hydrogen atom) and a compound 3 in which $X^1$ is Cl (chlorine atom), $R^2$ is Ac (acetyl group) and $R^4$ is Ac (acetyl group).

EXAMPLES

The process for producing the compound of the present invention will now be described in detail by way of examples, but the present invention is not limited by these examples. In the following description, purity was expressed by a GC area percentage.

Example 1

1) Preparation of
N-[(5-acetyl-2-chlorophenyl)methyl]acetamide
(Compound Number 3): Invention According to
[1])

36.7 g (0.2 moles) of N-[(2-chlorophenyl)methyl]acetamide was dissolved in 60 mL of dichloromethane and 80.0 g (0.6 moles) of aluminum chloride was added at 5 to 30° C. over 30 minutes, and then 31.4 g (0.4 moles) of acetyl chloride was added dropwise at the same temperature over 30 minutes.

The mixture was aged at room temperature for one hour, heated to a reflux temperature over 15 minutes and then aged under reflux for 12 hours. After the completion of the reaction, the resulting reaction solution was poured into water and extracted three times with 50 mL of toluene, and then the solvent was distilled off under reduced pressure. After cooling the residue, the precipitated crystal was collected by filtration, washed with toluene and dried to obtain 24.5 g (yield: 54.3%, purity: 99.4%) of the objective compound (melting point: 93.1 to 93.7° C.).

$^1$H-NMR (CHCl$_3$-d$_1$, 300 MHz) δ=2.0 (s, 3H, NHCO C$\underline{H}_3$), 2.6 (s, 3H, Ph-COCH$_3$), 4.6 (d, 2H, CH$_2$, J=6.0 Hz), 6.1 (br, s, 1H, N$\underline{H}$COCH$_3$), 7.5 (d, 1H, Ph ring, J=8.2 Hz), 7.8 (dd, 1H, Ph ring, J=2.2 8.2 Hz), 8.0 (d, 1H, Ph ring, J=2.2)

MS (GC-MS) m/z=225 (M$^+$), 190 (base)

Example 2

Preparation of N-[(5-acetyl-2-chlorophenyl)methyl] methoxycarboxyamide (A): Preparation of 1-[3-(aminomethyl)-4-chlorophenyl]ethan-1-one (Compound Number 1) (Invention According to [6])

20.0 g (0.089 moles) of N-[(5-acetyl-2-chlorophenyl) methyl]acetamide obtained in Example 1 was dissolved in 55 g of 50% sulfuric acid, followed by heating to a reflux temperature over 30 minutes and further aging under reflux for 15 hours.

After the completion of the reaction, the resulting solution was poured into water and 45 mL of toluene was added, and then the aqueous solution was made basic (pH=about 12.0) with 25% sodium hydroxide. After extracting twice with 45 mL of toluene, the solvent was distilled off under reduced pressure to obtain the titled compound (purity: 99.2%) substantially quantitatively.

MS (GC-MS) m/z=182 (M$^+$−1), 140 (base)

(B): Preparation of N-[(5-acetyl-2-chlorophenyl) methyl]methoxycarboxyamide (Invention According to [7])

17.1 g (0.089 moles) of 1-[3-(aminomethyl)-4-chlorophenyl]ethan-1-one obtained in Example 2-(A) was dissolved in 44.3 mL of toluene and then charged (mixed) with 14.7 g (0.107 moles) of potassium carbonate, followed by dropwise addition of 9.2 g (0.098 moles) of methyl chlorocarbonate at 5 to 20° C. over 30 minutes and further aging at room temperature for 3 hours.

After the completion of the reaction, the resulting reaction solution was poured into water and the solvent was distilled off under reduced pressure. After cooling the residue, the precipitated crystal was collected by filtration, washed with toluene and dried to obtain 19.3 g (yield: 90.2%, purity: 99.8%) of the objective compound (melting point: 108.1° C.).

$^1$H-NMR (CHCl$_3$-d$_1$, 300 MHz) δ=2.6 (s, 3H, Ph-COCH$_3$), 3.7 (s, 3H, COOCH$_3$), 4.5 (d, 2H, CH$_2$, J=6.3 Hz), 5.3(br, s, 1H, NH), 7.5 (d, 1H, Ph ring, J=8.3 Hz), 7.8 (dd, 1H, Ph ring, J=2.1 8.3 Hz), 8.0 (s, 1H, Ph ring)

MS (GC-MS) m/z=241 (M$^+$), 206 (base)

Example 3

Preparation of N-[(5-acetyl-2-chlorophenyl)methyl] methoxycarboxyamide (A): Preparation of N-[(2-chlorophenyl)methyl]acetamide: General Formula (1)

42.8 kg (0.3 kmoles) of (2-chlorophenyl)methylamine was dissolved in 118.3 kg of dichloromethane and 32.2 kg (0.315 kmoles) of acetic anhydride was added dropwise at 20 to 40° C. over 1.5 hours, followed by aging at room temperature for 30 minutes. After the completion of the reaction, 60 kg of water was added 55.2 kg of an aqueous 25% sodium hydroxide solution was added dropwise at 20 to 40° C. over 20 minutes. The organic layer was partitioned to obtain 169.9 kg of a dichloromethane solution of N-[(2-chlorophenyl)methyl]acetamide.

(B): Preparation of N-[(5-acetyl-2-chlorophenyl)methyl]acetamide (Compound Number 3): Invention According to [1]

To 169.9 kg of the dichloromethane solution of N-[(2-chlorophenyl)methyl]acetamide obtained in Example 3-(A), 47.1 kg (0.6 moles) of acetyl chloride was added and 108.0 kg (0.81 kmoles) of aluminum chloride was added at 15 to 30° C. over 1.5 hours. After dichloromethane was distilled off was distilled off under normal pressure until the temperature reaches 50° C. over 2 hours, the mixture was aged for 6 hours (objective product: other position isomers=76.75%:1.65%; GC area %). After the completion of the reaction, the resulting solution was added dropwise to 450 kg of water at 15 to 35° C. over 2 hours. The solution was extracted twice with 90 kg of dichloromethane and 40 kg of dichloromethane to obtain 199.8 kg of a dichloromethane solution of N-[(5-acetyl-2-chlorophenyl)methyl] acetamide.

(C): Preparation of 1-[3-(aminomethyl)-4-chlorophenyl]ethan-1-one (Compound Number 1) (Invention According to [6])

To 199.8 kg of a dichloromethane solution of N-[(5-acetyl-2-chlorophenyl)methyl]acetamide obtained in Example 3-(B), 90 kg of water and 46 kg (0.45 kmoles) of 98% sulfuric acid were added. Dichloromethane was distilled off under normal pressure over 1.5 hours until the inner temperature reaches 100° C., followed by aging for 6 hours. After the completion of the reaction, the reaction solution was cooled to 50° C. over 20 minutes and 90 kg of water and 105 kg of toluene were added. After cooling, 212 kg of an aqueous 25% sodium hydroxide solution was added dropwise at 15 to 25° C. over 2.5 hours. After heating to 40° C. over 30 minutes, the organic layer was partitioned to obtain a toluene solution of 1-[3-(aminomethyl)-4-chlorophenyl] ethan-1-one.

(D): Preparation of N-[(5-acetyl-2-chlorophenyl) methyl]methoxycarboxyamide (Invention According to [7])

To the toluene solution of 1-[3-(aminomethyl)-4-chlorophenyl]ethan-1-one obtained in Example 3-(C), 180 kg of water and 45.7 kg (0.33 kmoles) of potassium carbonate were added, followed by mixing, dropwise addition of 28.4 kg (0.3 kmoles) of methyl chlorocarbonate at 15 to 25° C. over one hour and further aging at room temperature for one hour. After the completion of the reaction, the reaction solution was heated to 60° C. over 30 minutes and the organic layer was partitioned. To the resulting toluene solution of N-[(5-acetyl-2-chlorophenyl)methyl]methoxycarboxyamide, 150 kg of water was added and toluene was distilled off under normal pressure over 2 hours. The residue was cooled to 50° C. over 30 minutes and 39 kg of toluene was added, followed by cooling to 10° C. over 1.5 hours. The precipitated crystal was collected by filtration and then washed with 13 kg of toluene. The resulting crystal was dried to obtain 49.1 kg (yield: 67.7%; on the basis of (2-chlorophenyl)methylamine, purity: 94.5%) of N-[(5-acetyl-2-chlorophenyl)methyl]methoxycarboxyamide.

INDUSTRIAL APPLICABILITY

As described above, according to the present invention, the problems of the prior art are solved and a method, which is useful for the preparation of a carbamate derivative, is provided.

According to the present invention, for example, there are provided a process for producing a carbamate derivative represented by the general formula (3), which is useful in the preparation of a carbamate derivative represented by the general formula (6) as a useful intermediate for a carbamate-based agricultural or horticultural bactericide, a process for producing the carbamate derivative represented by the general formula (6), and a novel intermediate compound.

According to the present invention, for example, the carbamate derivative represented by the general formula (6) as a useful intermediate for a carbamate-based bactericide in good yield and purity by a simple operation. Therefore, the method of the present invention has particularly high industrial utility value.

The invention claimed is:

1. A process for producing a benzylamine derivative represented by the general formula (3):

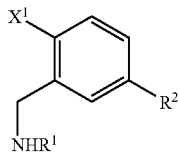

(3)

wherein $X^1$, $R^1$ and $R^2$ are as defined below, which comprises reacting a benzyl derivative represented by the general formula (1):

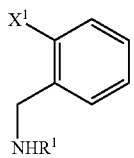

(1)

wherein $X^1$ represents a halogen atom and $R^1$ represents an acyl group, with a haloacyl compound represented by the general formula (2):

wherein $X^2$ represents a halogen atom and $R^2$ represents an acyl group, in the presence of Lewis acid.

2. A process for producing a carbamate derivative represented by the general formula (6):

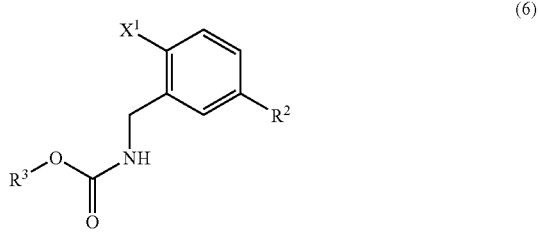

(6)

wherein $X^1$, $R^2$ and $R^3$ are as defined below, which comprises reacting a benzyl derivative represented by the general formula (1):

(1)

wherein $X^1$ represents a halogen atom and $R^1$ represents an acyl group, with a haloacyl compound represented by the general formula (2):

wherein $X^2$ represents a halogen atom and $R^2$ represents an acyl group, in the presence of Lewis acid to obtain a benzylamine derivative represented by the general formula (3):

(3)

wherein $X^1$, $R^1$ and $R^2$ are as defined above, hydrolyzing the benzylamine derivative to obtain an amino derivative represented by the general formula (4):

(4)

wherein $X^1$ and $R^2$ are as defined above, and reacting the amino derivative with a haloformic acid ester represented by the general formula (5):

(5)

wherein $X^3$ represents a halogen atom and $R^3$ represents an alkyl group, in the presence of a base.

3. An acylbenzylamine derivative represented by the general formula (7):

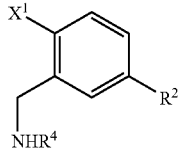 (7)

wherein $X^1$ represents a halogen atom, $R^2$ represents an acyl group, selected from the group consisting of $C_1$-$C_7$ linear aliphatic acyl groups, $C_1$-$C_7$ branched aliphatic acyl groups, $C_3$-$C_6$ cycloalkylcarbonyl groups, and unsubstituted aromatic acyl groups, and and $R^4$ represents a hydrogen atom or an acyl group.

4. The acylbenzylamine derivative of claim 3, wherein $R^2$ represents an acyl group selected from the group consisting of $C_1$-$C_7$ linear aliphatic acyl groups, $C_{1\text{-}C7}$ branched aliphatic acyl groups, and $C_3$-$C_6$ cycloalkylcarbonyl groups, and R4 represents a hydrogen atom.

5. The acylbenzylamine derivative of claim 3, wherein $R^2$ represents an acyl group selected from the group consisting of $C_1$-$C_7$ linear aliphatic acyl groups, $C_1$-$C_7$ branched aliphatic acyl groups, $C_3$-$C_6$ cycloalkylcarbonyl groups, and unsubstituted aromatic acyl groups, and $R^4$ represents an acyl group.

* * * * *